United States Patent [19]
Rosenstatter

[11] Patent Number: 6,015,290
[45] Date of Patent: Jan. 18, 2000

[54] DENTAL HANDPIECE

[76] Inventor: Otto Rosenstatter, Matzing 105, A-5164 Seeham, Austria

[21] Appl. No.: 09/217,969

[22] Filed: Dec. 22, 1998

[51] Int. Cl.[7] ................. A61C 3/00; A61C 1/10
[52] U.S. Cl. ............................................... 433/29
[58] Field of Search ................ 433/29, 114, 118, 433/119, 126, 127, 131, 132, 133

[56] References Cited

U.S. PATENT DOCUMENTS

| | | | |
|---|---|---|---|
| 4,642,738 | 2/1987 | Meller | 433/29 |
| 4,673,351 | 6/1987 | Luiset et al. | 433/29 |
| 4,680,011 | 7/1987 | Boinot | 433/29 |
| 4,711,630 | 12/1987 | Durr | 433/29 |
| 4,902,225 | 2/1990 | Lohn | 433/29 |

Primary Examiner—John J. Wilson
Attorney, Agent, or Firm—Wenderoth, Lind & Ponack, L.L.P.

[57] ABSTRACT

Dental handpiece comprising a headpiece in which a treatment tool for preparation of a place being treated can be fitted and, a handgrip which has a rear end and a forward end to which a forward region, which has a longitudinal axis, is adjacent. Wherein the headpiece is attachable on the forward end of the handgrip. The handpiece further comprises a lighting means, arranged in the forward region of the handgrip, with an incandescent lamp which has a longitudinal axis. The longitudinal axis of the incandescent lamp is orientated substantially parallel to the longitudinal axis of the forward region of the handgrip. Laterally adjacent to the incandescent lamp, a light outlet is provided in the handgrip. Laterally on the incandescent lamp or in the light outlet of the handgrip laterally adjacent to the incandescent lamp, a lens is provided for focusing the light emitted from the incandescent lamp onto the place being treated.

5 Claims, 3 Drawing Sheets

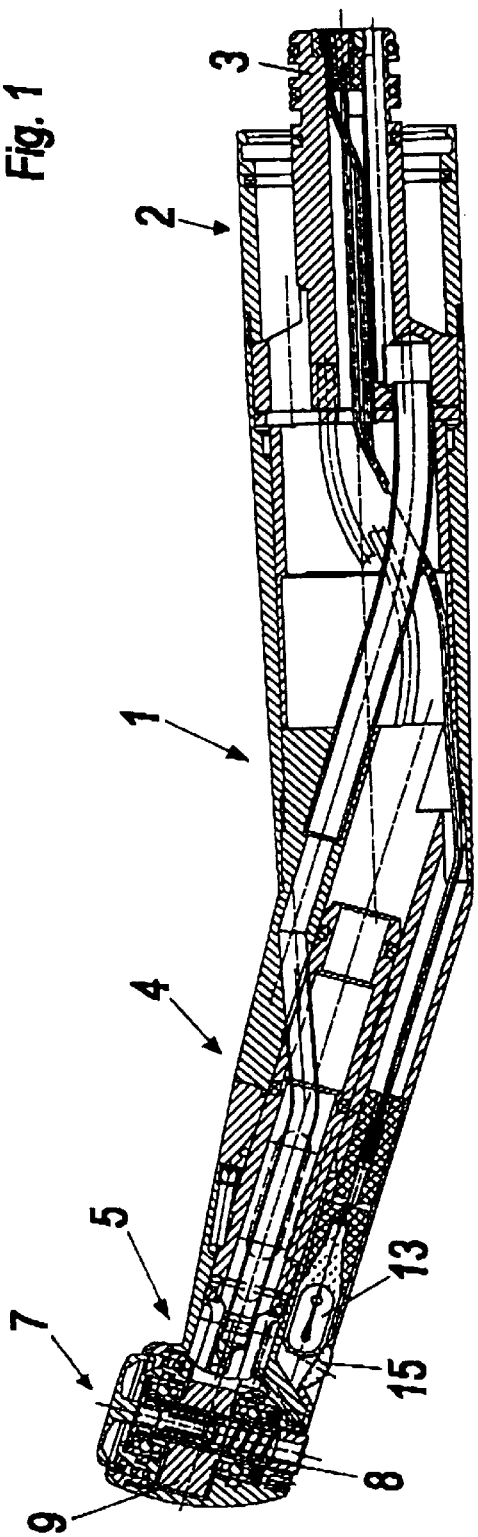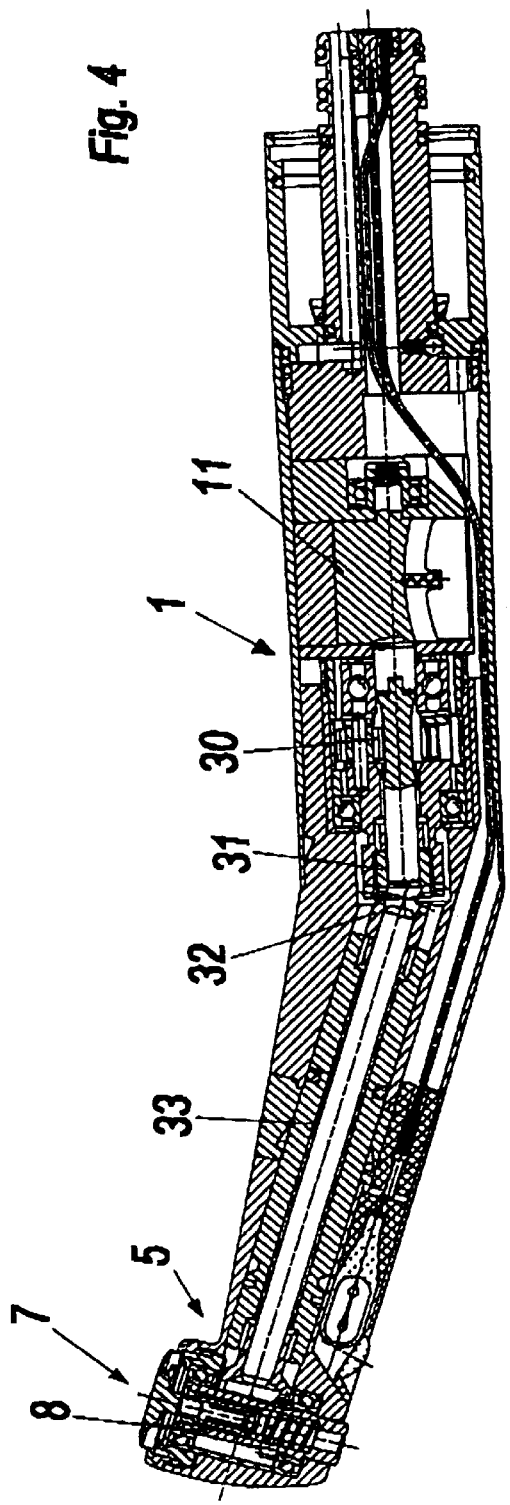

DENTAL HANDPIECE

BACKGROUND OF THE INVENTION

The invention relates to a dental handpiece with a headpiece for receiving a treatment tool, a handgrip for manipulating the handpiece having a forward end to which the headpiece is attached, and a lighting means with an incandescent lamp arranged in the forward region of the handgrip. The longitudinal axis of the incandescent lamp is orientated substantially parallel to the longitudinal axis of the forward region of the handgrip, and laterally adjacent to the incandescent lamp there is provided a light outlet in the handgrip.

With conventional dental handpieces, the light sources are mostly arranged in the rear region of the handpiece and the light is conducted to the forward end of the handpiece by means of optical fibres. Such handpieces have the disadvantage that when the light is fed into the optical fibres, and when the light is transmitted, there are losses in light intensity. Moreover, when optical fibres are used, there is the difficulty of orientating their light-emitting ends in a suitable manner in the direction of the place being treated. Because of their fragility, they can only be slightly bent, and the angle of bending permissible is generally insufficient to orientate their ends precisely onto the place being treated.

A handpiece without light conduction is known from AT-PS 384 546. In the forward part of the handgrip for this handpiece an incandescent lamp is arranged, and the light emitted by this incandescent lamp is deflected by an optical element in front of the incandescent lamp, in the form of a prism or mirror, in the direction of the place being treated. The low light yield is disadvantageous, because only a small region of the solid angle of the light radiated from the incandescent lamp actually reaches the place being treated. The prism used causes further light losses.

A handpiece of the type described in the introduction is known from U.S. Pat. No. 4,711,630. In contrast to AT-PS 384 546, the incandescent lamp is arranged still further forward, and a part of the light emitted by it reaches the place being treated directly by means of a slit-shaped light outlet arranged laterally adjacent to the incandescent lamp in the handgrip. A further part of the light emitted by the incandescent lamp is conducted by means of a lens at the forward end of the incandescent lamp and optical fibres in the headpiece, and from there is likewise radiated in the direction of the place being treated. In this way, although the light yield is increased compared to the handpiece of AT-PS 384 546, nevertheless the construction is complex, and therefore expensive. The space needed for the optical fibres in the headpiece is also disadvantageous, and makes it larger. Thus, the whole handpiece becomes less manageable.

SUMMARY OF THE INVENTION

The object of the invention is to obtain a high power at illumination of the place being treated with a handpiece a simple and easy to handle construction. In accordance with the invention, this is achieved in that laterally adjacent to the incandescent lamp, in the light outlet of the handgrip, or laterally on the incandescent lamp, there is provided a lens for focusing the light radiated from the incandescent lamp onto the place being treated.

In this way, the light radiated from the incandescent lamp is concentrated onto the place being treated at the solid angle at which the lens is positioned, and a high density of illumination of the place being treated is obtained without the light conducting system in the treatment headpiece having to be reconfigured.

BRIEF DESCRIPTION OF THE DRAWINGS

Further advantages and details of the invention will be explained hereinafter with reference to the attached drawings, in which FIG. 1 is a section through the central longitudinal plane of a handpiece according to a first embodiment of the invention;

FIG. 4 is a longitudinal section corresponding to FIG. 1, of another embodiment of the handpiece;

DETAILED DESCRIPTION OF THE INVENTION

Figure 2:
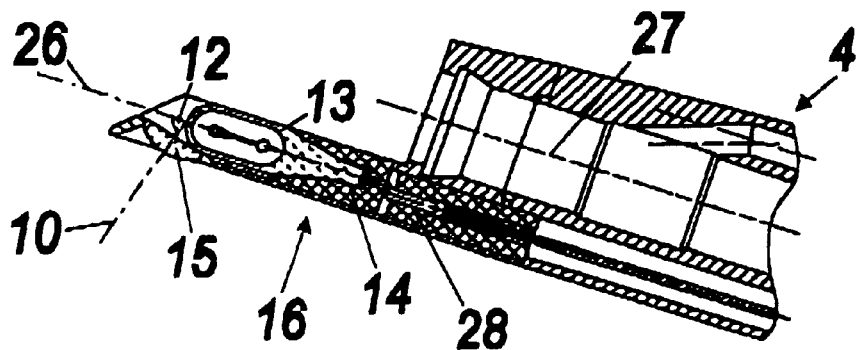
FIG. 2 is the forward region of the handgrip shown in FIG. 1, with the headpiece removed.
Figure 3:
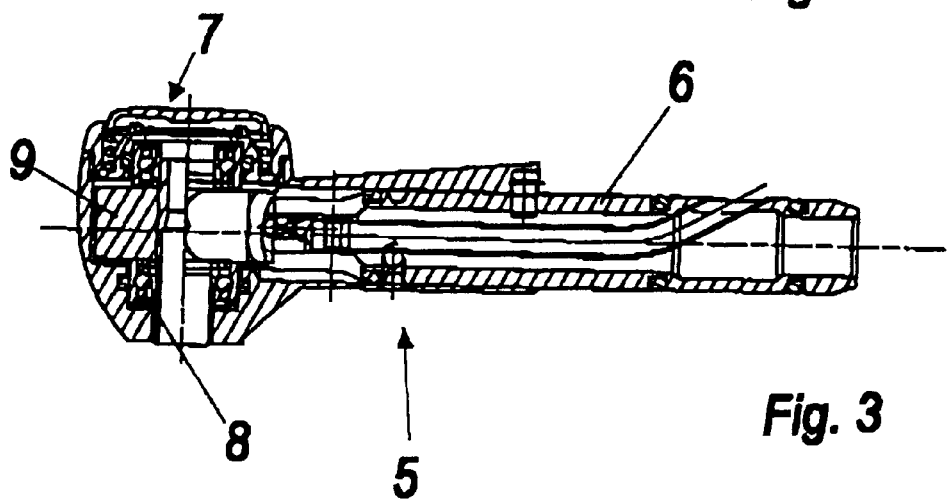
FIG. 3 is a headpiece which can be fitted onto the handgrip of FIG. 2.

The handpiece shown in FIGS. 1 to 3 of a first embodiment of the invention has a handgrip 1, the rear region 2 of which is provided with a coupling pin 3. The handgrip 1 can be connected in a rotatable manner to a conventional adaptor (not shown) by the coupling pin 3 for connection to a supply hose. The forward region 4 of the handgrip which is arranged at an angle to the rear region 2 has a bore 29 with a longitudinal axis 27 for receiving a headpiece 5. The headpiece 5 includes a connection piece 6 which can be pushed into the bore 29, and it can be connected via a conventional locking means (not shown and described in more detail here) to the forward region 4 of the handgrip 1. The headpiece 5 further includes an angled tool attachment headpiece 7 for receiving a treatment tool (not shown). Additionally, the tool attachment headpiece 7 has a clamp sleeve 8 driven by a compressed-air driven turbine 9.

The handpiece includes a lighting means with an incandescent lamp 13 arranged in the forward region of the handgrip 1, which is preferably a halogen lamp. The lamp is fixed, preferably integrally moulded, with a lamp holder 14. The longitudinal axis 26 of this incandescent lamp 13 is thus orientated substantially parallel to the longitudinal axis 27 of the forward region 4 of the handgrip 1. The incandescent lamp 13 is inserted in a projection 16 at the forward end of the handgrip 1. This projection 16 has a cylindrical hollow space which forms a receiver for the incandescent lamp 13 and the lamp holder 14 connected to it. Contact pins project from the back of the lamp holder 14 for electrically connecting the incandescent lamp 13. These contact pins can be inserted into sockets 28 provided in the end face on the end of the cylindrical bore in the projection 16 and are connected to electrical leads for power supply. A slit (not shown in the drawings) in the top side of the projection 16 serves for the removal and changing of the incandescent lamp 13.

Laterally adjacent to the incandescent lamp 13, in a preferably circular aperture in the projection 16, there is provided a lens 15, whereby a light outlet is formed for the light emitted from the incandescent lamp. The light passing through the lens 15 is suitably focused by it and thus concentrated on the place being treated. In this way, with a simple construction a particularly good illumination of the place being treated is obtained. The optical axis 10 of the lens 15 (which is generally perpendicular to the lens) is at an angle 12 of more than 30°, and preferably more than 60°, to the longitudinal axis 26 of the incandescent lamp 13. The angle will then advantageously be smaller than or equal to 90°. The focal length of the lens 15 is selected so that the light incident on the lens is suitably concentrated on the place being treated (so, for example, a cone of light with a 1 cm diameter is incident upon the place being treated).

A further light outlet can be provided on the forward end face of the projection 16. This light outlet can be used when a straight headpiece is fitted onto the handgrip, in order to conduct light through the straight headpiece to light the place being treated, lying in front of the headpiece.

In the embodiment shown in FIG. 4 of the handpiece, in the headpiece 5, instead of a turbine, a compressed-air driven blade motor 11 is provided in the handgrip 1, the rotation of which is transferred via a planetary gear mechanism 30 from a pinion 31 driven by the motor to a pinion 32 which is connected to a drive shaft mounted in the headpiece 5, and via the drive shaft further to the rotatably mounted clamp sleeve 8 in the angled tool attachment headpiece 7. With this, the lighting system can thus remain completely unaltered.

The lighting system according to the invention could likewise be used with a hand piece with an electric motor.

Figure 5:
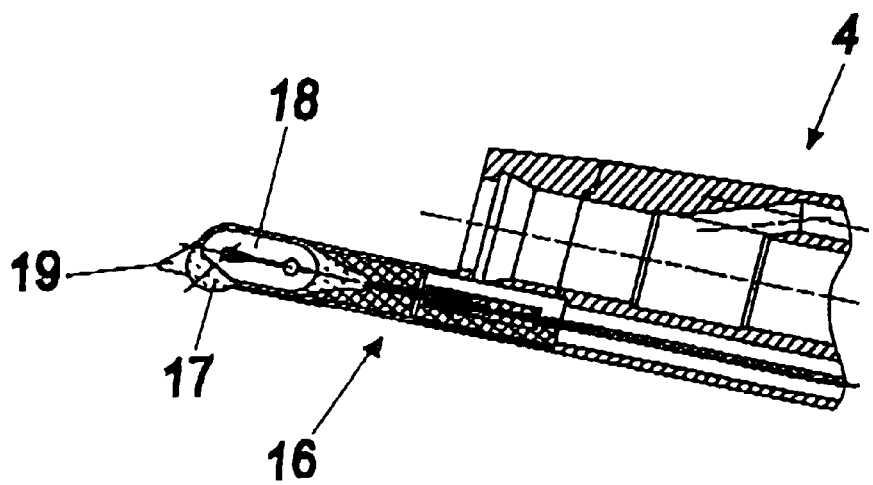
FIG. 5 is a longitudinal section through the forward region of a handgrip of a further embodiment of the invention.
Figure 6:
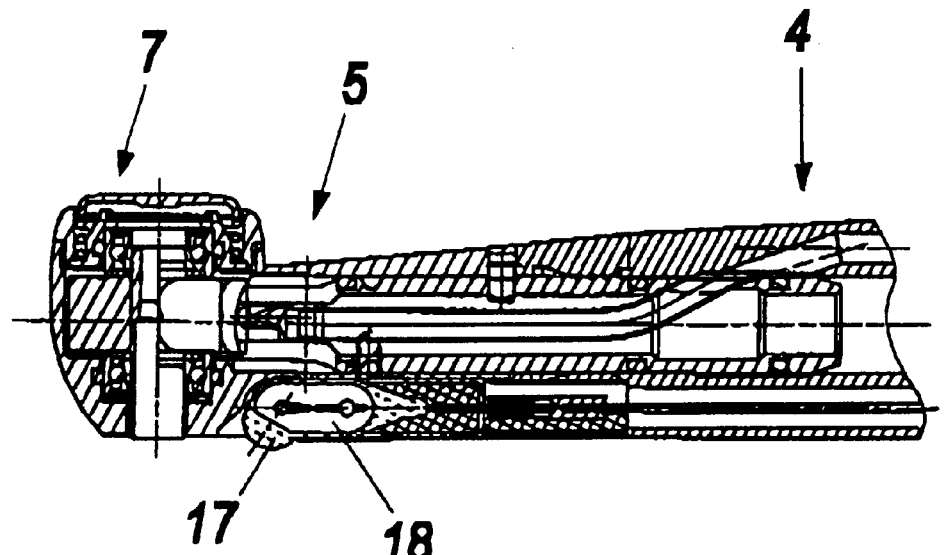
FIG. 6 is the handgrip of FIG. 5 with a headpiece fitted to it.
Figure 7:
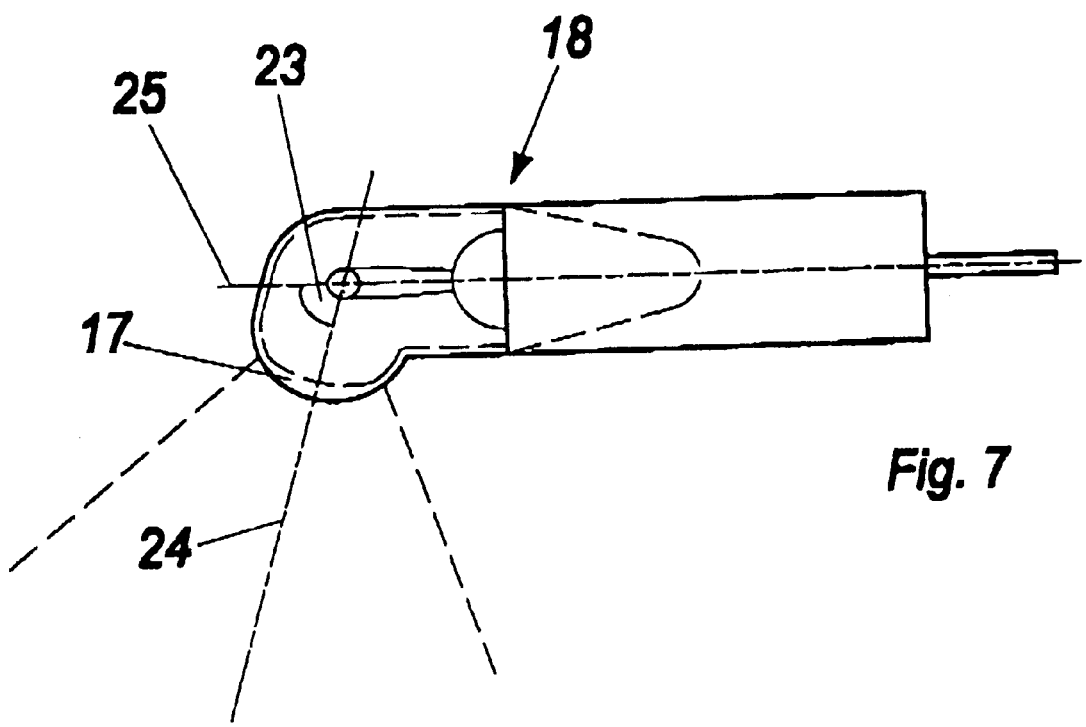
FIG. 7 is a side view of an incandescent lamp with a laterally arranged lens for use with the embodiment of FIGS. 5 and 6.

A further embodiment of the invention is shown in FIGS. 5 to 7. In this case, a lens 17 is arranged directly laterally on the incandescent lamp 18. In the projection 16 of the handgrip, a cut-out 19 is provided in the region of this lens 17, which forms a light outlet. The lens 17 can partly pass through this cut-out 19 and consequently partly protrude from the projection 16 of the handgrip. Again, the light emitted from the incandescent lamp 18 is concentrated through the lens 17 onto the place being treated.

The optical axis 24 of the lens 17 of the incandescent lamp 18 is again at an angle 23 of more than 30°, preferably more than 60°, and advantageously less than or equal to 90°. In the embodiment shown, the angle 23 is approximately 75°. The focal length of the lens 17 is selected such that the light incident upon the lens is concentrated in a suitable manner on the place being treated (so that, for example, a cone of light with a 1 cm diameter is incident upon the place being treated).

I claim:

1. A dental handpiece comprising:

a headpiece in which a treatment tool for preparation of a place being treated can be fitted;

a handgrip having a rear region and a forward region, the forward region having a longitudinal axis, wherein the headpiece is attachable to the forward region of the handgrip; and a lighting member arranged in the forward region of the handgrip, the lighting member including an incandescent lamp having a longitudinal axis, wherein the longitudinal axis of the incandescent lamp is substantially parallel to the longitudinal axis of the forward region of the handgrip, wherein a light outlet is provided in the handgrip laterally adjacent to the incandescent lamp, and wherein a lens for focusing the light emitted from the incandescent lamp onto the place being treated is provided laterally on the incandescent lamp or in the light outlet of the handgrip laterally adjacent to the incandescent lamp.

2. The dental handpiece according to claim 1, wherein the incandescent lamp is arranged in a projection on the forward region of the handgrip so that the incandescent lamp is facing the headpiece.

3. The dental handpiece according to claim 1, wherein the headpiece can be removably connected to the handgrip by a quick-release lock.

4. The dental handpiece according to claim 1, wherein the lens has an optical axis, and the optical axis of the lens is arranged at an angle of more than 30° with respect to the longitudinal axis of the incandescent lamp.

5. The dental handpiece according to claim 4, wherein the angle between the optical axis of the lens and the longitudinal axis of the incandescent lamp is less than or equal to 90°.

* * * * *